(12) United States Patent
Chung et al.

(10) Patent No.: US 10,925,534 B2
(45) Date of Patent: Feb. 23, 2021

(54) SKIN MEASUREMENT DEVICE AND CONTROL METHOD THEREFOR

(71) Applicant: LG ELECTRONICS INC., Seoul (KR)

(72) Inventors: Jungho Chung, Seoul (KR); Dongwon Kim, Seoul (KR)

(73) Assignee: LG ELECTRONICS INC., Seoul (KR)

(*) Notice: Subject to any disclaimer, the term of this patent is extended or adjusted under 35 U.S.C. 154(b) by 572 days.

(21) Appl. No.: 15/557,333

(22) PCT Filed: Sep. 2, 2015

(86) PCT No.: PCT/KR2015/009236
§ 371 (c)(1),
(2) Date: Sep. 11, 2017

(87) PCT Pub. No.: WO2016/153132
PCT Pub. Date: Sep. 29, 2016

(65) Prior Publication Data
US 2018/0049689 A1    Feb. 22, 2018

(30) Foreign Application Priority Data
Mar. 20, 2015  (KR) .................. 10-2015-0039078

(51) Int. Cl.
*A61B 5/00* (2006.01)
*A61N 7/00* (2006.01)
(Continued)

(52) U.S. Cl.
CPC ............ *A61B 5/441* (2013.01); *A61B 5/0036* (2018.08); *A61B 5/0059* (2013.01);
(Continued)

(58) Field of Classification Search
CPC ... A61B 5/0059; A61B 5/6843; A61B 5/7207; A61B 5/743; A61B 5/0066; A61B 5/441;
(Continued)

(56) References Cited

U.S. PATENT DOCUMENTS 6,263,227 B1 * 7/2001 Boggett ............... A61B 5/0261
356/39
2002/0022868 A1 * 2/2002 Lenderink ............ A61B 5/0066
607/88
(Continued)

FOREIGN PATENT DOCUMENTS

CN     101801274 A    8/2010
CN     102499755 A    6/2012
(Continued)

*Primary Examiner* — Bo Joseph Peng
(74) *Attorney, Agent, or Firm* — Birch, Stewartm Kolasch & Birch, LLP

(57) ABSTRACT

The present invention relates to a skin measurement device capable of measuring information related to the skin. The skin measurement device capable of transmitting and receiving data to and from a skin treatment device, according to one embodiment of the present invention, comprises: a sensing unit formed so as to sense information related to the skin; and a control unit for controlling the sensing unit such that the sensing unit senses information related to certain skin, on the basis of contact between the skin measurement device and the certain skin, wherein the sensing unit is formed so as to emit light on the certain skin and to sense the information related to the certain skin on the basis of light reflected from the certain skin.

5 Claims, 6 Drawing Sheets

(51) Int. Cl.
*A61N 5/06* (2006.01)
*A61N 5/067* (2006.01)

(52) U.S. Cl.
CPC .......... *A61B 5/0066* (2013.01); *A61B 5/6844* (2013.01); *A61B 5/743* (2013.01); *A61N 7/00* (2013.01); *A61B 5/4836* (2013.01); *A61B 5/6843* (2013.01); *A61B 5/7207* (2013.01); *A61N 5/0616* (2013.01); *A61N 2005/067* (2013.01); *A61N 2005/0626* (2013.01); *A61N 2007/0034* (2013.01)

(58) Field of Classification Search
CPC ................ A61B 5/6844; A61B 5/4836; A61N 2005/067; A61N 2005/0626; A61N 2007/0034; A61N 5/0616; A61N 7/00
See application file for complete search history.

(56) References Cited

U.S. PATENT DOCUMENTS

| | | | |
|---|---|---|---|
| 2005/0075547 A1* | 4/2005 | Wang | A61B 5/0066 600/316 |
| 2007/0060819 A1 | 3/2007 | Altshuler et al. | |
| 2007/0100245 A1* | 5/2007 | Kashima | A61B 5/0261 600/504 |
| 2007/0129711 A1 | 6/2007 | Altshuler et al. | |
| 2007/0239142 A1 | 10/2007 | Altshuler et al. | |
| 2013/0253338 A1 | 9/2013 | Kang et al. | |
| 2013/0281865 A1 | 10/2013 | Kang et al. | |

FOREIGN PATENT DOCUMENTS

| | | |
|---|---|---|
| CN | 103268499 A | 8/2013 |
| CN | 103415755 A | 11/2013 |
| CN | 103536275 A | 1/2014 |
| CN | 203408032 U | 1/2014 |
| CN | 103565410 A | 2/2014 |
| CN | 104287721 A | 1/2015 |
| JP | 2001-37741 A | 2/2001 |
| JP | 2006-385 A | 1/2006 |
| JP | 2009-509140 A | 3/2009 |
| JP | 2009-153727 A | 7/2009 |
| JP | 2014-176047 A | 9/2014 |
| KR | 10-2006-0115478 A | 9/2006 |
| KR | 10-0866258 B1 | 11/2008 |
| KR | 10-2012-0128427 A | 11/2012 |
| KR | 10-2014-0022607 A | 2/2014 |
| KR | 10-1440325 B1 | 9/2014 |
| WO | WO 2013/056126 A2 | 4/2013 |

\* cited by examiner

SKIN MEASUREMENT DEVICE AND CONTROL METHOD THEREFOR

CROSS REFERENCE TO RELATED APPLICATIONS

This application is the National Phase of PCT International Application No. PCT/KR2015/009236, filed on Sep. 2, 2015, which claims priority under 35 U.S.C. 119(a) to Patent Application No. 10-2015-0039078, filed in Republic of Korea on Mar. 20, 2015, all of which are hereby expressly incorporated by reference into the present application.

TECHNICAL FIELD

The present invention relates to a skin measurement device capable of measuring information related to skin, and more particularly, to a skin measurement device capable of measuring information related to skin using a light interference phenomenon, and a method of controlling the same.

BACKGROUND ART

As interest in cosmetics grows larger, customers for dermatologic procedures (skin treatment), for example, treatment, care or management for skin, are increasing, and accordingly development of a skin treatment device which treats, cares or manages skin is being actively carried out.

The related art skin treatment devices are based on laser, high frequency, ultrasound and the like. In addition, the related art skin treatment device classifies skin characteristics into several types through clinical tests at a development stage, and includes several modes that vary setting values thereof according to the respective skin characteristics.

These setting values may include an output level, a wavelength, a frequency, depth of focus, and the like of laser, high frequency or ultrasonic wave.

However, users who receive skin treatments have different skin characteristics. Accordingly, when the skin treatment is performed only in those modes using the related art skin treatment device, different effects of the treatment on the user basis are inevitable. In addition, since the skin treatment is performed only in a few modes previously stored in the related art skin treatment device, some users have a problem that side effects are caused due to excessive treatment. In addition, since a selection of the mode included in the related art skin treatment device is also decided according to a doctor's subjective opinion, accuracy of the skin treatment is lowered.

Accordingly, in recent years, development of methods for performing skin treatment optimized for each user and devices (skin measurement devices) capable of measuring skin-related information to guide optimized skin treatment procedures of skin treatment devices is actively undergoing.

DISCLOSURE OF THE INVENTION

One aspect of the present invention is to provide a skin measurement device, capable of measuring skin-related information such that each user can receive an optimized skin treatment, and a method for controlling the same.

Another aspect of the present invention is to provide a skin measurement device, capable of measuring various types of skin-related information in an optimized manner, and a method of controlling the same.

To achieve these and other advantages and in accordance with the purpose of this specification, as embodied and broadly described herein, there is provided a skin measurement device capable of performing data transmission and reception with a skin treatment device, the measurement device including a sensing unit configured to sense information related to skin, and a controller configured to control the sensing unit to sense information related to a specific (or certain) skin when the skin measurement device is brought into contact with the specific skin, wherein the sensing unit emits light to the specific skin, and senses the information related to the specific skin based on reflected light from the specific skin.

In one embodiment of the present invention, the information related to the specific skin sensed by the sensing unit may include at least one of light reflectance at a surface of the specific skin, a light attenuation rate at the epidermis of the specific skin, a light attenuation rate at the dermis of the specific skin, and an epidermal thickness.

In one embodiment of the present invention, the sensing unit may include a light source, and may be configured to emit at least part of the light emitted from the light source to the specific skin, emit light other than the at least part of the light to a mirror provided therein, and sense the information related to the specific skin using interference between light reflected from the specific skin and light reflected from the mirror.

In an embodiment of the present invention, the controller may perform a plurality of sensing operations and extract the information related to the specific skin based on a plurality of sensing results of the plurality of sensing operations.

In the embodiment of the present invention, the plurality of sensing operations may be performed, in response to the skin measurement device being moved due to an external force while being in contact with the specific skin.

In one embodiment of the present invention, the controller may merge the plurality of sensing results sensed at a plurality of points on the specific skin by the movement of the skin measurement device in a preset manner, and extract the information related to the specific skin using the merged plurality of sensing results. Each of the plurality of sensing results may include light reflection intensity information corresponding to a skin depth for each point of the specific skin. The preset manner may be to merge the plurality of sensing results such that light reflection intensity information at a surface of the specific skin of each light reflection intensity information can coincide with each other.

In one embodiment of the present invention, the controller may transmit the sensed information related to the specific skin to the skin treatment device based on satisfaction of a preset condition. The preset condition may be at least one of a case where an elapsed time after the skin measurement device is brought into contact with the specific skin exceeds a preset time, a case where the skin measurement device is moved by a preset distance in the contact state with the specific skin, and a case where the skin measurement device in the contact state with the specific skin is separated from the specific skin.

In an embodiment of the present invention, the skin measurement device may further include a display unit configured to output an image guiding a selection of a part of a body. The controller may transmit the sensed information related to the specific skin together with information corresponding to at least part of the image when the skin measurement device is brought into contact with the specific skin after the at least part of the image is selected.

To achieve these and other advantages and in accordance with the purpose of this specification, as embodied and broadly described herein, there is provided a method for controlling a skin measurement device capable of performing data transmission and reception with a skin treatment device, the method including sensing information related to a specific skin in response to the skin measurement device being brought into contact with the specific skin, and transmitting the sensed information related to the specific skin to the skin treatment device based on satisfaction of a preset condition. The sensing may be configured to emit light to the specific skin and sense the information related to the specific skin based on reflected light from the specific skin. The information related to the specific skin may include at least one of light reflectance at a surface of the specific skin, a light attenuation rate at the epidermis of the specific skin, a light attenuation rate at the dermis of the specific skin, and an epidermal thickness.

In one embodiment of the present invention, the sensing may include performing a sensing operation at each of a plurality of points on the skin, in response to the skin measurement device being moved due to an external force while being in contact with the specific skin, merging a plurality of sensing results sensed at the plurality of points such that light reflection intensity information at a surface of the specific skin of light reflection intensity information included in each of the plurality of sensing results can coincide with each other, and extracting the information related to the specific skin using the merged plurality of sensing results.

In one embodiment of the present invention, the transmitting may be configured to transmit the sensed information related to the specific skin to the skin treatment device based on satisfaction of a preset condition. The preset condition may be at least one of a case where an elapsed time after the skin measurement device is brought into contact with the specific skin exceeds a preset time, a case where the skin measurement device is moved by a preset distance in the contact state with the specific skin, and a case where the skin measurement device in the contact state with the specific skin is separated from the specific skin.

In one embodiment of the present invention, the method may further include, before the sensing step, outputting an image guiding a selection of a part to a body on a display unit. The transmitting may be configured to transmit the sensed information related to the specific skin together with information corresponding to at least part of the image when the skin measurement device is brought into contact with the specific skin after the at least part of the image is selected.

Effects of the Invention

As described above, according to the present invention, a skin measurement device of the present invention can measure information related to a specific skin to be treated, namely, light reflectance on a surface of the skin, a light attenuation rate at the epidermis of the skin, a light attenuation rate at the dermis of the skin, an epidermal thickness and the like and transmit the measured information to a skin treatment device, which may enable an optimized skin treatment at the skin treatment device. Accordingly, the present invention provides an effect that an optimized skin treatment can be performed by recognizing (detecting, determining) a skin characteristic for each user.

In addition, the skin measurement device according to the present invention can extract information related to the skin based on sensing results obtained at a plurality of points of the skin, which may allow an extraction of more accurate skin conditions, i.e., the information related to the skin.

In addition, the skin measurement device according to the present invention can transmit the skin-related information to the skin treatment device, in response to satisfaction of a preset condition. Thus, according to the present invention, an effect of enhancing user convenience in performing a skin treatment can be obtained.

In addition, the skin measurement device according to the present invention can output an image guiding a selection of a part of a body. Also, when the skin measurement device is brought into contact with the skin after at least part of the image is selected, the skin measurement device can transmit the skin-related information to the skin treatment device together with information corresponding to the selected at least part of the image. Accordingly, the present invention can provide a new user interface that allows information related to the portion (skin) of the body measured using the skin measurement device to be output on or stored in the skin treatment device.

DETAILED DESCRIPTION OF THE INVENTION

Figure 1:
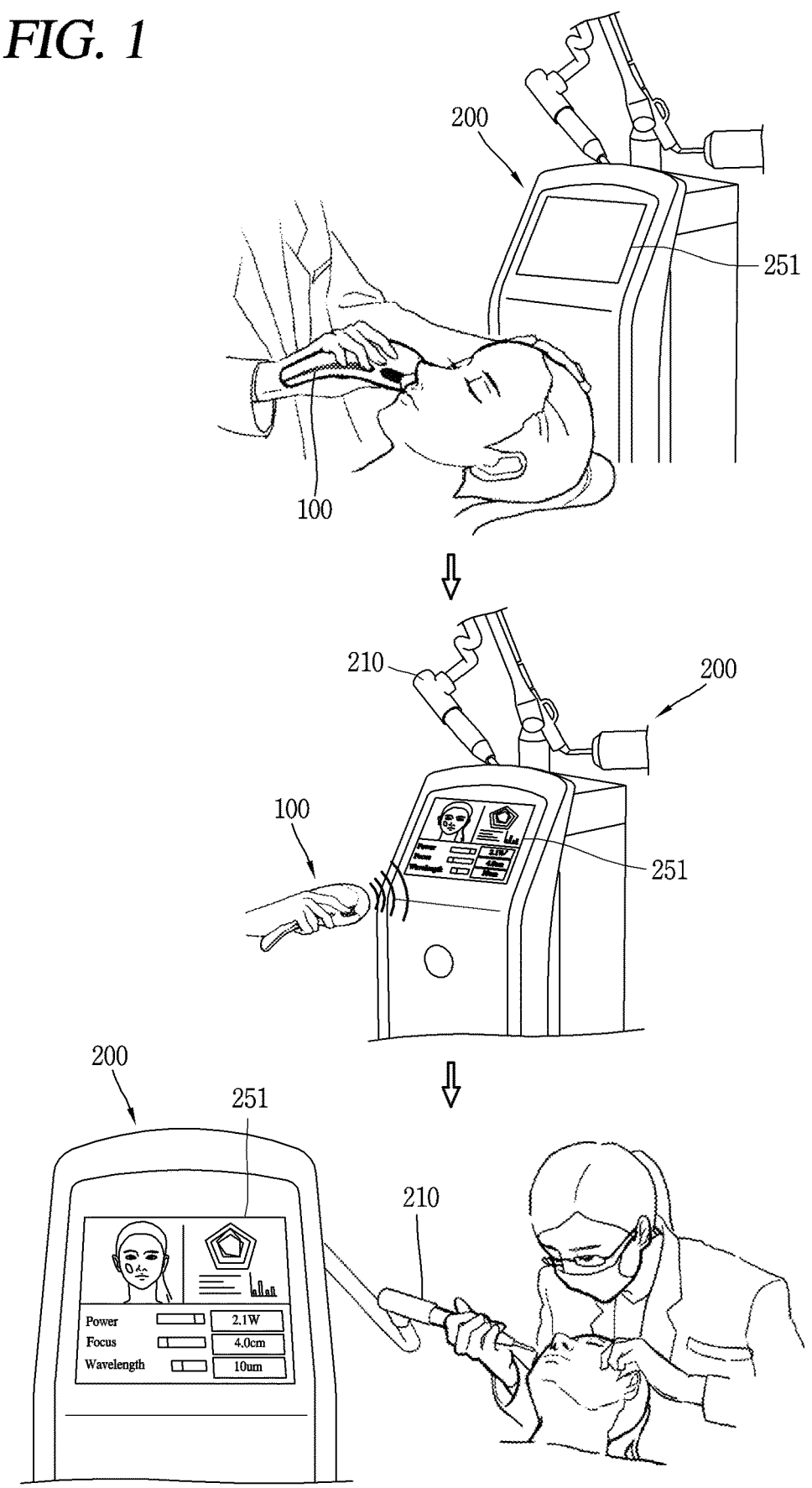
FIG. 1 is a block diagram illustrating a skin measurement device and a skin treatment device in accordance with one embodiment of the present invention.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In describing the present disclosure, if a detailed explanation for a related known function or construction is considered to unnecessarily divert the gist of the present disclosure, such explanation has been omitted but would be understood by those skilled in the art. The accompanying drawings are used to help easily understand the technical idea of the present disclosure and it should be understood that the idea of the present disclosure is not limited by the accompanying drawings. The idea of the present disclosure should be construed to extend to any alterations, equivalents and substitutes besides the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the another element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Hereinafter, when explaining the accompanying drawings, when at least two images in one drawing (FIG. N) are illustrated in the form of 2 by 2, an image shown at an upper left is referred to as a "first drawing", an image shown at an upper right is referred to as "second drawing", an image shown at a lower right is referred to as "third drawing", and an image shown at a lower left is referred to as "fourth drawing".

In addition, when at least two images are illustrated in a line from top to bottom in one drawing (FIG. N), those images are referred to as "first drawing, second drawing, . . . ," sequentially from a top image.

Also, when at least two images are illustrated in a line from left to right in one drawing (FIG. N), the images are referred to as "first drawing, second drawing, . . . ," sequentially from the leftmost image.

A skin measurement device described herein may be configured to sense (extract, detect, measure, etc.) information related to skin of a subject (e.g., a person, etc.). The skin measurement device may have a form of a probe.

A probe refers to a tool or device used for the purpose of measuring, probing, monitoring, sensing, extracting, detecting, or measuring a target or subject (or information related to the target or subject, a status of the target). In addition, the probe may be understood as a detector for measuring (sensing, extracting, detecting, etc.) the status of the subject (target) to be measured, without a change if possible.

The skin measurement device of the present invention, which can have the form of the probe, may be included as one component of the skin treatment device or may exist as a separate component.

It will be readily apparent to those skilled in the art that the configuration according to the embodiment described in this specification can also be applied to devices, which are capable of measuring information (or status) related to all subjects (e.g., objects, animals, plants, etc.), if excluding a case of being applicable merely to a skin measurement device.

Referring to FIG. 1, FIG. 1 is a conceptual view illustrating a skin measurement device and a skin treatment device according to one embodiment of the present invention.

A skin treatment system according to one embodiment of the present invention may include a skin measurement device 100 and a skin treatment device 200. The skin treatment device 200 may be a device that directly performs treatment (care or management) on skin using laser, high frequency, or ultrasound.

The skin measurement device 100 may be configured to guide the skin treatment device 200 to set elements, such as wavelength, intensity, focal position and the like of laser, high frequency or ultrasonic wave, which is optimized for skin to be treated, when performing the skin treatment using the skin treatment device 200.

The skin measurement device 100 and the skin treatment device 200 may be configured to transmit and receive data. For this purpose, each of the skin measurement device 100 and the skin treatment device 200 may be provided with a communication unit for performing wired/wireless communication.

As illustrated in a first drawing of FIG. 1, the skin measurement device 100 may measure (sense) skin-related information (or skin condition). Here, the skin measurement device 100 may sense the skin-related information using light. Specifically, the skin measurement device 100 according to the present invention may sense the skin-related information using an Optical Coherence Tomography (OCT) Technique (Description of the OCT technique will be given later in more detail with reference to FIG. 2B).

The skin-related information may include surface reflectance of the skin, an epidermal thickness of the skin, a light attenuation ratio in the epidermis, a light attenuation ratio in the dermis, an average light attenuation ratio in the epidermis and the dermis, and the like. In addition, the skin-related information may further include an amount of melanin contained in the skin.

As illustrated in a second drawing of FIG. 2, the skin measurement device 100 may transmit the sensed skin-related information to the skin treatment device 200. Here, the skin measurement device 100 may transmit the measured skin-related information based on satisfaction of a preset condition.

The preset condition may be at least one of a case where an elapsed time after the skin measurement device 100 is brought into contact with a specific (certain) skin exceeds a preset time, a case where the skin measurement device 100 is moved by a preset distance in a contact state with the skin, a case where the skin measurement device 100 in the contact state with the skin is separated from the skin, and a case where a user request is received. The skin measurement device 100 may transmit the sensed skin-related information to the skin treatment device 200 based on a reception of a skin transmission request from the skin treatment device 200.

The skin measurement device 100 may be configured in an independent form separated from the skin treatment device 200, or in a form connected to the skin treatment device 200. When the skin measurement device 100 is separate from the skin treatment device 200, the skin measurement device 100 may transmit the skin-related information to the skin treatment device 200 using wireless communication.

When the skin measurement device 100 is connected to the skin treatment device 200 by wire, the skin measurement device 100 may transmit the skin-related information to the skin treatment device 200 through the wire.

As illustrated in a third drawing of FIG. 1, the skin treatment device 200 may perform treatment on the skin. The skin treatment device 200 may include a treatment probe 210 that emits at least one of laser, high frequency and ultrasonic wave, a display module 251 that outputs at least one of output information (e.g., wavelength, intensity (strength), a focal position, etc.) of laser (high frequency or ultrasonic wave), and various screen information related to the skin treatment device (or skin treatment), a memory that stores therein a table in which skin-related information and the output information relating to the laser are associated with each other, a communication unit, a power supply unit, and a controller (or control unit) that controls those components.

Here, the skin treatment device 200 may set (determine) the output information (output value, setting value) of the laser based on the skin-related information received from the skin measurement device 100. As described above, the skin-related information received from the skin measurement device 100 may include the surface reflectance of the skin, the epidermal thickness of the skin, the light attenuation rate in the epidermis, the light attenuation rate in the dermis, the average light attenuation rate in the epidermis and the dermis, and the like.

The memory of the skin treatment device 200 may store therein output information of the laser optimized for each value of the skin-related information in an associating manner. The output information of the laser associated with the skin-related information may be called 'table'. The table may be received from an external device (e.g., a server or a terminal) or may exist on the skin treatment device 200 from the time of shipment of the skin treatment device 200.

The controller (or control unit) of the skin treatment device 200 may set (determine) the output information of the laser based on the table stored in the memory, when the skin-related information is received from the skin measurement device 100.

When information corresponding to a portion of a body (information related to the portion of the body) is transmitted together with the sensed skin-related information from the skin measurement device 100, the controller of the skin treatment device 200 may store the transmitted information in the memory on a user basis or a time basis. That is, the skin treatment device 200 according to the present invention may store information in a dividing manner on a user basis, a skin area basis and a time basis, which may result in constructing a database for a progress of the skin treatment per individual user, and more effectively recognizing treatment effects for the skin.

Meanwhile, the skin measurement device 100 may be configured to transmit the output information of the laser to the skin treatment device 200, similar to the skin treatment device 200, as well as transmitting the sensed skin-related information to the skin treatment device 200. To this end, the memory of the skin measurement device 100 may store therein the output information of the laser associated with each skin-related information, namely, the table. Likewise, the table may be received from an external device (e.g., a server or a terminal) or may exist on the skin measurement device 100 from the time of shipment of the skin measurement device 100.

The controller of the skin measurement device 100 may extract the output information of the laser using the table, and transmit at least one of the skin-related information and the output information of the laser according to a user request or under the control of the controller.

In addition, the skin measurement device 100 may transmit the sensed skin-related information together with information corresponding to a portion of a body to the skin treatment device 200 (related contents will be described in more detail later with reference to FIG. 7).

With this configuration, the present invention may decide the output information of the laser used for the skin treatment in the skin treatment device, based on the skin-related information sensed using the skin measurement device. Therefore, the present invention can perform skin treatment optimized for each skin even if characteristics (conditions) of the skin are different for each user and for each skin area.

Hereinafter, with reference to FIGS. 2A and 2B, a skin measurement device and a method of sensing skin-related information by the skin measurement device according to the present invention will be described in more detail.

Figure 2A:
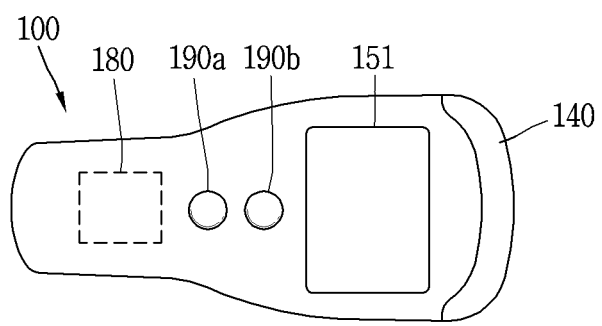
FIG. 2A is a block diagram illustrating a skin measurement device in accordance with one embodiment of the present invention.
Figure 2B:
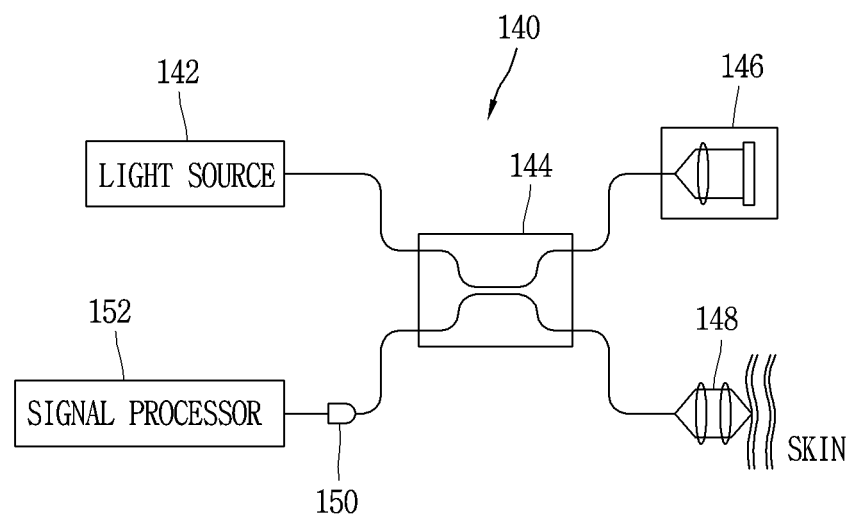
FIG. 2B is a conceptual view illustrating a sensing unit provided in a skin measurement device in accordance with one embodiment of the present invention.

FIG. 2A is a conceptual view illustrating a skin measurement device in accordance with one embodiment of the present invention, and FIG. 2B is a conceptual view illustrating a sensing unit provided in the skin measurement device according to one embodiment of the present invention.

Referring to FIG. 2A, the skin measurement device 100 of the present invention may include a communication unit, an input unit, a sensing unit 140, an output unit, an interface unit, a memory, a controller 180, a power supply unit, and the like. In implementing the skin measurement device 100 using those components, greater or fewer components may be added.

In more detail, among those components, the communication unit 200 may include one or more modules which permit wired/wireless communications between the skin measurement device 100 and the skin treatment device 200, between the skin measurement device 100 and a wireless communication system, between the skin measurement device 100 and another terminal, or between the skin measurement device 100 and an external server. The communication unit 110 may include one or more modules that allow the skin measurement device 100 to be connected to at least one network.

The communication unit may include at least one of a wireless Internet module, a short distance communication module, and a wired communication module.

The input unit 120 may include a camera 121 or an image input unit for inputting an image signal, a microphone 122 or an audio input unit for inputting an audio signal, and user input units 190*a* and 190*b* (for example, touch keys, mechanical keys, and the like) for allowing a user to input information. Data (for example, audio, video, image, and the like) may be obtained by the input unit 120 and may be analyzed and processed as user's control commands.

The user input units 190*a* and 190*b* are provided for receiving control commands from the user and may control the skin measurement device 100 to cope with information input through the user input units 190*a* and 190*b*. The user input unit 123 may include one or more of a mechanical input element (for example, a mechanical key, a button located on a front and/or rear surface or a side surface of the digital signage 100, a dome switch, a jog wheel, a jog switch, and the like), and a touch-sensitive input element, among others.

For example, one 190*a* of the user input units may be a power button for turning on or off the skin measurement device 100. In addition, another user input unit 190*b* different from the one user input unit 190*a* may be a button associated with at least one of a function of starting sensing of the skin-related information, a function of stopping sensing of the skin-related information, and a function of transmitting the sensed skin-related information to the skin treatment device 200.

The sensing unit 140 may sense the skin-related information using an optical coherence tomography (OCT) technique. The sensing unit 140 may operate according to the control of the controller 180. (Description of the sensing unit 140 will be given in more detail later with reference to FIG. 2B).

The output unit is provided for generating a visual, audible or tactile output. The output unit may include at least one of a display unit 151, an audio output module, a haptic module 153, and an optical output module. The display unit 151 may have an inter-layered structure or an integrated structure with a touch sensor in order to implement a touch screen. The touch screen may provide an output interface between the skin measurement device 100 and a user, as well as functioning as a user input unit which provides an input interface between the skin measurement device 100 and the user.

The display unit 151 may display various screen information that can be output on the skin measurement device 100. The various screen information may include screen information related to measurement of the skin-related information (for example, a graphic object associated with a measurement start function, notification information indicating that the measurement is in progress, a graphic object associated with a measurement stop function, a function of transmitting measured information to the skin treatment device, an image for guiding the user to select the measured skin-related information or a portion of a body, a graphic object for guiding an area of the image to which a touch is applied, etc.), status information related to the skin measurement device (for example, time, battery level or power level), and the like.

The interface unit serves as an interface with various types of external devices that are coupled to the skin measurement device 100. The interface unit, for example, may include any of external charger ports, wired/wireless data ports, memory card ports, ports for connecting a device having an identification module, audio input/output (I/O) ports, video I/O ports, earphone ports, and the like. The skin measurement device 100 may perform assorted control functions associated with a connected external device, in response to the external device being connected to the interface unit.

The memory is configured to store data to support various functions or features of the skin measurement device 100. The memory 170 may be configured to store application programs (or applications) executed in the skin measurement device 100, data or instructions for operations of the skin measurement device 100, and the like.

Further, after the skin-related information is sensed, the sensed information may be stored (or temporarily stored) in the memory. Also, the memory may store a table in which the output information of the laser and skin-related information are associated with each other.

In the meantime, the application programs which are stored in the memory and installed on the skin measurement device 100 may be executed by the controller 180 to perform operations (or functions) for the skin measurement device 100.

The controller 180 typically functions to control an overall operation of the skin measurement device 100, in addition to the operations associated with the application programs. The controller 180 may provide information or functions appropriate for a user by processing or storing in the memory signals, data, information and the like, which are input or output through those components, or may execute the application programs stored in the memory.

In addition, the controller 180 may control a combination of at least two of those components included in the skin measurement device 100 to activate the application program.

The power supply unit may be configured to receive external power or internal power in order to supply appropriate power required for operating the components included in the skin measurement device 100. The power supply unit may include a battery, and the battery may be configured as an embedded battery or a detachable battery.

At least part of the components may cooperatively operate to implement an operation, a control or a control method of a skin measurement device according to various embodiments disclosed herein. Also, the operation, the control or the control method of the skin measurement device may be implemented on the skin measurement device by an activation of at least one application program stored in the memory.

Hereinafter, the sensing unit 140 of the skin measurement device 100 will be described in more detail with reference to FIG. 2B.

The skin measurement device 100 according to an embodiment of the present invention may use an Optical Coherence Tomography (OCT) technique to extract skin-related information. An OCT system using the OCT technique is configured based on broadband light sources and low-coherence interferometers (for example, the Michaelson type or the Mach Zehnder type), to acquire changes in backscattered light, generated due to scattering of skin tissues (for example, epidermis, dermis, etc.), at different depth.

The sensing unit 140 may emit light to a skin brought into contact with the skin measurement device 100, and sense information related to the contacted skin based on light reflected from the contacted skin. In detail, the sensing unit 140 may emit at least part of light emitted from a light source 142 provided therein to the contacted skin, and emit light other than the at least part of the light to a mirror 146 provided therein. The sensing unit 140 may thus sense the information related to the contacted skin using interference between light reflected from the contacted skin and light reflected from the mirror 146.

To this end, the sensing unit 140 of the skin measurement device 100, as illustrated in FIG. 2B, may include a light source 142, a beam splitter 144, a mirror 146, a contact portion 148 (or a probe) brought into contact with a specific skin, a detector 150, a signal processor 152, and the like.

The light source 142 generates any one light. In this case, the light source 142 may be a low coherent light source that emits light with low coherence. The light generated by the light source 142 may be incident on the beam splitter 144.

The beam splitter 144 divides the incident light into at least two parts. Specifically, the beam splitter 144 divides low coherent light incident from the light source 142 into two parts, such that one of the two parts of light is incident on the mirror 146 and another part of the light, different from the one part of light, is incident on the contact portion 148.

The mirror 146 may be configured to reflect light incident from the beam splitter 144 so as to be incident on the beam splitter 144 again. The mirror 146 may be referred to as a reference system or a reference mirror and may be shifted or axially scanned along at least one direction to generate a path difference. As the mirror 146 is shifted, a phase of the light reflected by the mirror 146 and returning to the beam splitter 144 may be changed. This may affect interference between light reflected from the mirror and light reflected back from the skin (for example, constructive interference or destructive interference).

The contact portion 148 refers to a portion of the sensing unit 140 to be brought into contact with the skin, and may be referred to as a probe. The contact portion 148 may be configured to transmit the light incident from the beam splitter 144 to the contacted skin and to cause the light reflected from the skin to be incident on the beam splitter 144 again.

The skin may generally consist of epidermis, dermis and subcutaneous fat layers. Here, the light incident on the skin from the beam splitter 144 is reflected to have different path differences and light intensities according to depth of the skin. The light is reflected at different intensities because at least part of the incident light is absorbed by the skin.

The beam splitter 144 may divide light into the light reflected from the mirror 146 and the light reflected from the skin, respectively. Specifically, the beam splitter 144 may be formed such that at least part of the light reflected from the mirror and at least part of the light reflected from the skin are incident on the detector 150.

The at least part of the light reflected from the mirror and the at least part of the light reflected from the skin cause an interference phenomenon therebetween. That is, constructive interference may occur when paths of the two lights match (coincide with) each other, and destructive interference may occur when the paths of the two lights do not match each other. Since the at least part of the light reflected from the skin generates a path difference due to depth of the skin, the sensing unit 140 (or the controller 180) may control the mirror to move to find a point where the path of the light reflected from the mirror and a path of light reflected at different depth match each other (i.e., a point where the constructive interference occurs). Intensity of a constructively-interfered signal at the point where the paths of light match each other may be referred to as a peak value.

The detector 150 may detect at least part of the light incident from the mirror and at least part of the light reflected from the skin, which are incident by being divided by the beam splitter 144, and then transmit signals corresponding to the detected light to the signal processor 152. Specifically, the detector 150 may acquire (convert) interference signals (for example, a peak value for each skin depth) of the at least part of the light reflected from the mirror and the at least part of the light reflected from the skin as (into) electric signals.

The signal processor 152 may acquire information related to the skin, specifically, skin depth-related information (for example, intensity (peak value) of reflected light for each skin depth), based on the signals transmitted from the detector 150. The signal processor 152 may be included in the sensing unit 140 or may be provided outside the sensing unit 140. The signal processor 152 may be separate from the controller 180 or may be the controller 180 itself (hereinafter, the signal processor 152 is the controller 180 for convenience of description).

The skin measurement device 100 of the present invention may extract skin-related information based on intensity of light reflected for each skin depth through the sensing unit 140.

Hereinafter, description will be given in more detail of a method of controlling a skin measurement device according to one embodiment of the present invention, which may include at least one of the aforementioned components, and a method of extracting skin-related information based on intensity of light reflected for each skin depth, with reference to the accompanying drawings.

Figure 3:
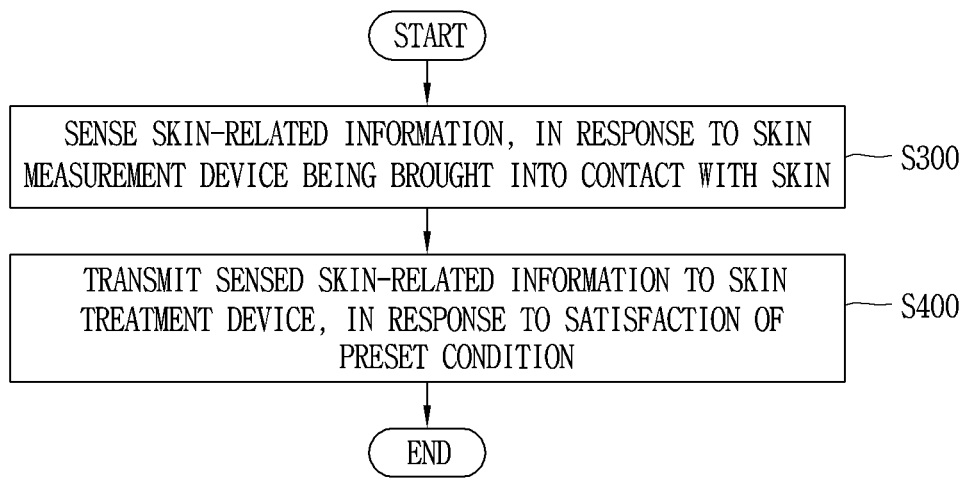
FIG. 3 is a flowchart illustrating a representative method of controlling a skin measurement device in accordance with the present invention.
Figure 4:
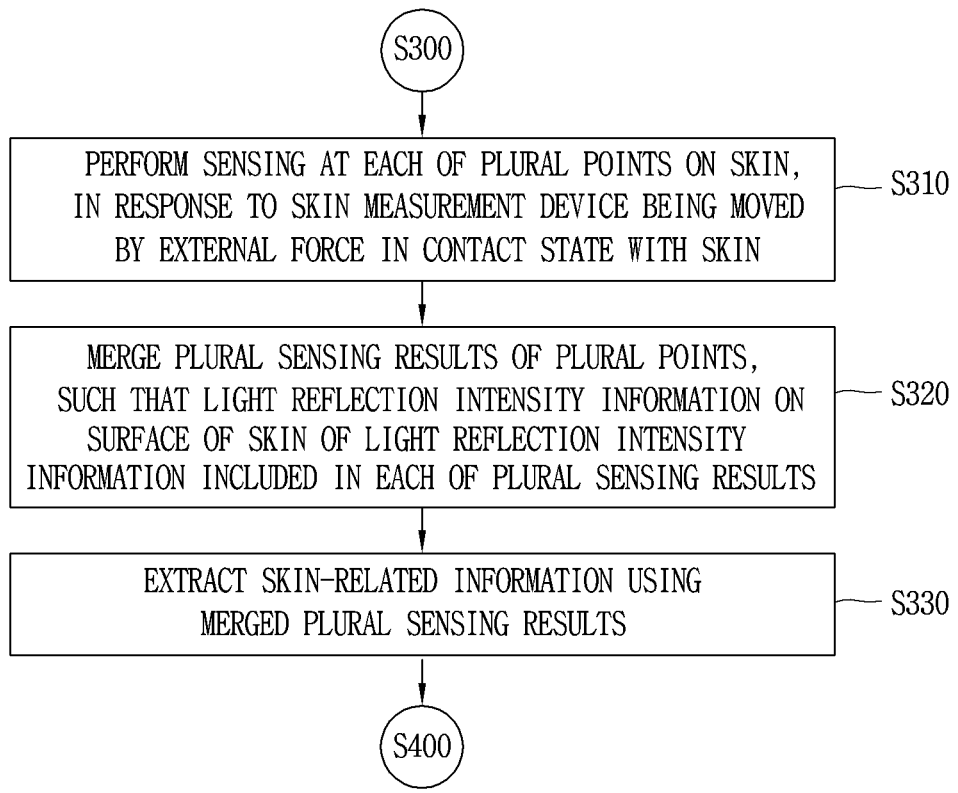
FIG. 4 is a flowchart illustrating in detail a method for sensing skin-related information illustrated in FIG. 3.

FIG. 3 is a flowchart typically illustrating a method of controlling a skin measurement device of the present invention, and FIG. 4 is a flowchart specifically illustrating a method of sensing skin-related information illustrated in FIG. 3.

Figure 5A:
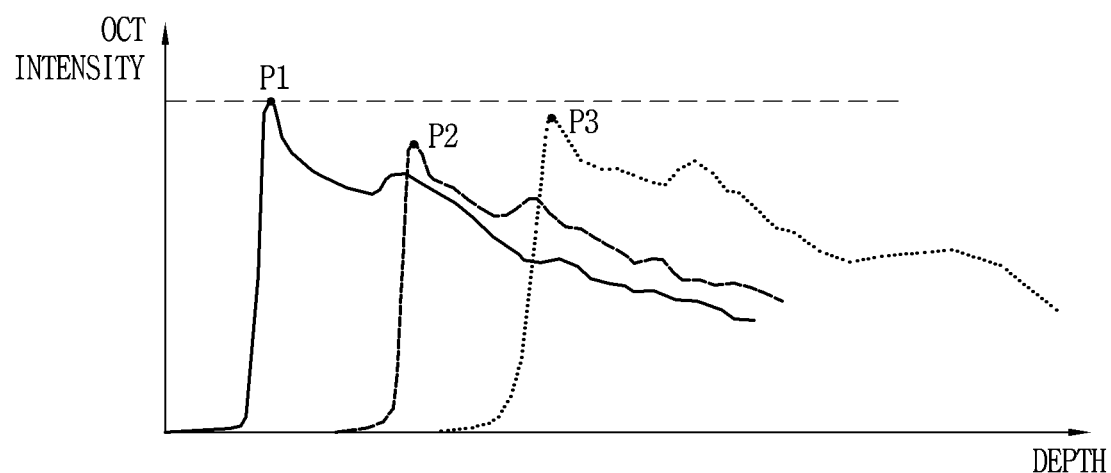
FIGS. 5A and 5B are conceptual views illustrating the control method illustrated in FIG. 4.
Figure 5B:
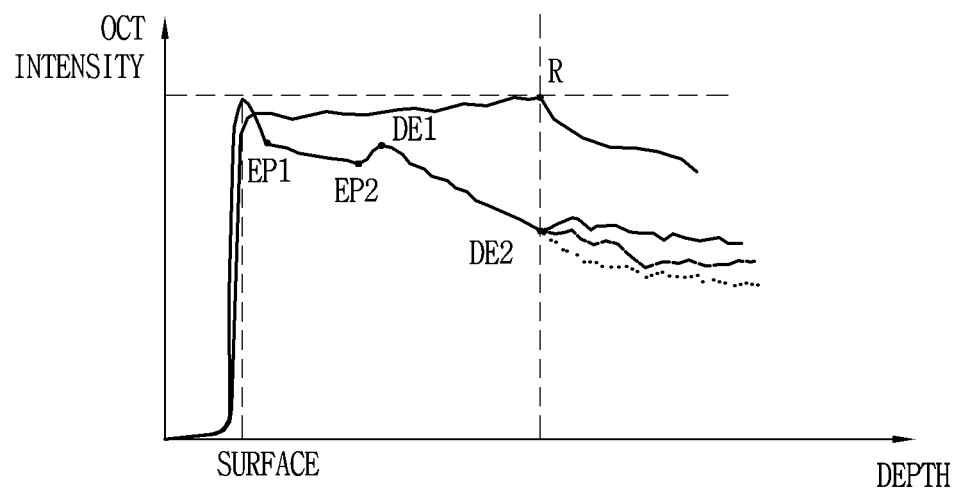
Figure 6:
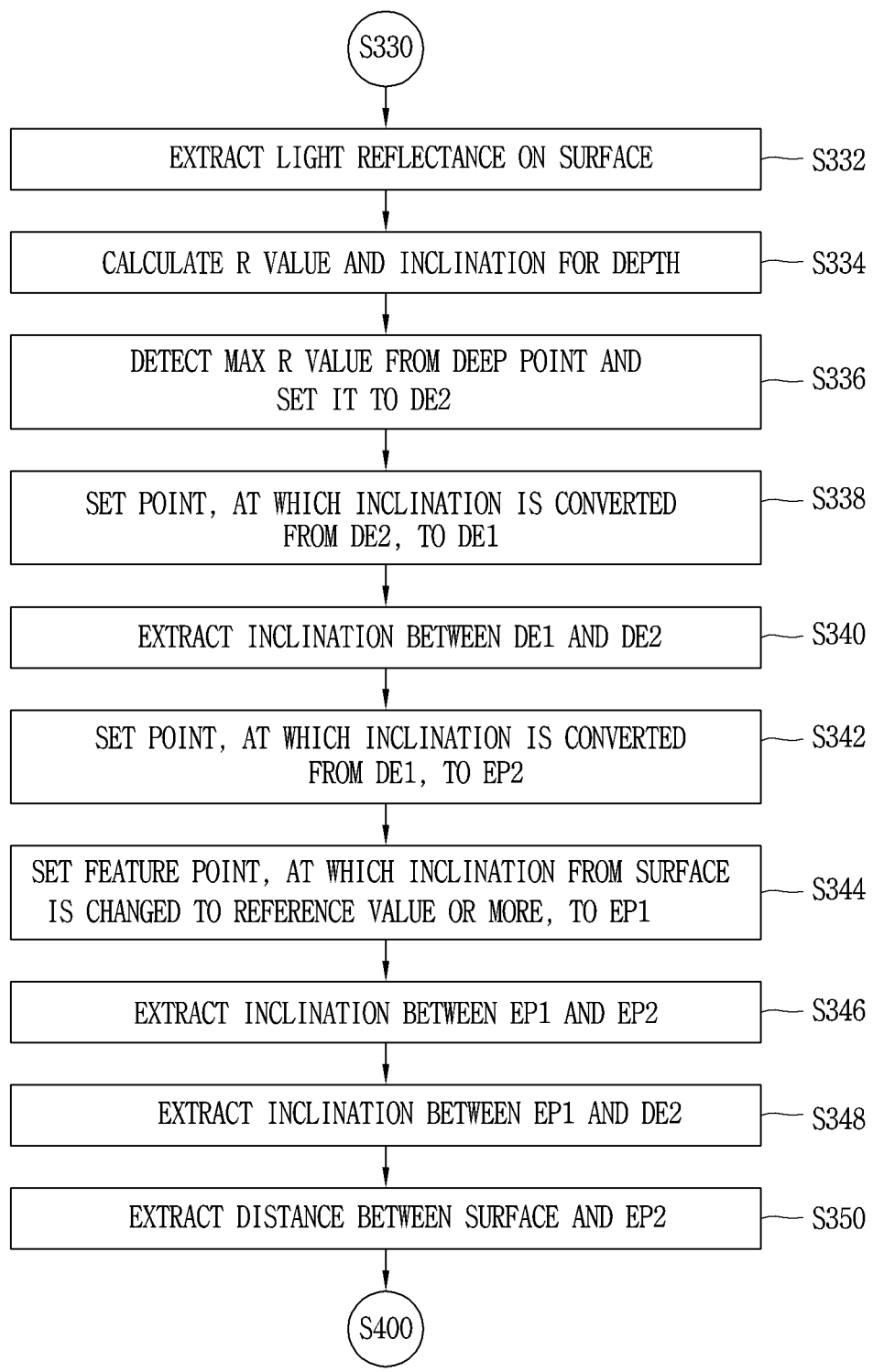
FIG. 6 is a flowchart illustrating a method of extracting skin-related information using a plurality of sensing results illustrated in FIG. 4.

FIGS. 5A and 5B are conceptual views illustrating the control method illustrated in FIG. 4, and FIG. 6 is a flowchart illustrating a method of extracting skin-related information using a plurality of sensing results illustrated in FIG. 4.

Referring to FIG. 3, in the present invention, when the skin measurement device 100 is brought into contact with a specific (or certain) skin, information related to the specific skin is sensed (S300). Specifically, the controller 180 may detect that the skin measurement device 100 is brought into contact with the specific skin. The sensing may be performed through the sensing unit 140. The controller 180 may control the sensing unit 140 to sense information related to the contacted skin when the skin measurement device 100 is in contact with the specific skin.

The sensing unit 140, as illustrated in FIG. 2B, may include a light source. At least part of light emitted from the light source may be output to the specific skin and light other than the at least part of the light may be output to the mirror provided in the sensing unit. Then, the sensing unit 140 may sense information related to the specific skin using interference between light reflected from the skin and light reflected from the mirror.

A method of sensing the skin-related information may be the method described in FIG. 2B. The information related to the specific skin may include surface reflectance of the skin, an epidermal thickness of the skin, a light attenuation rate in the epidermis of the skin, a light attenuation rate in the dermis of the skin, an average light attenuation rate in the epidermis and the dermis of the skin, and the like.

On the other hand, the controller 180 may sense the skin-related information in a preset manner. For example, the controller 180 may sense the skin-related information, continuously or at a period of a predetermined time, while the skin measurement device 100 is brought into contact with the skin.

As another example, the controller 180 may perform a plurality of sensing operations based on the fact that the skin measurement device 100 is moved by an external force in the contact state with the skin. For example, the controller 180 may control the sensing unit 140 to perform a sensing operation whenever the skin measurement device 100 is moved by a predetermined distance in the contact state with the specific skin, or when the movement of the skin measurement device 100 corresponds to a preset pattern.

As another example, the controller 180 may perform a sensing operation, in response to a user request, when the user request for the skin measurement device 100 is received. When the sensing is performed based on the user request, the controller 180 may perform sensing regardless of whether the skin measurement device 100 is in contact with the skin or not.

Thereafter, in the present invention, the skin measurement device 100 transmits the sensed skin-related information to the skin treatment device, based on that a preset condition is met (S400).

For example, once the skin-related information is sensed, the controller 180 may transmit the sensed skin-related information to the skin treatment device 200, based on at least one or a combination of a case where a time elapsed after the skin measurement device 100 is in contact with the skin exceeds a preset time, a case where the skin measurement device 100 is moved by a preset distance in the contact state with the skin, a case where the skin measurement device brought into contact with the skin is separated from the skin, a case where a movement of the skin measurement device 100 corresponds to a preset movement, and a case where a user request is received.

Here, the preset movement may include, for example, movement of the sensing unit 140 of the skin measurement device, which is brought into contact with the skin, toward the skin treatment device 200, or movement corresponding to a preset pattern.

Meanwhile, the skin measurement device 100 may also transmit the skin-related information to the skin treatment device 200 after the measurement (sensing) of the skin is completed, or transmit the skin-related information to the skin treatment device 200 in real time while performing the measurement on the skin.

The skin treatment device 200 may determine output information related to a laser used for the skin treatment on the skin, based on the skin-related information transmitted from the skin measurement device 100 (the method of determining the output information related to the laser will be understood by the details described in FIG. 1.

Hereinafter, description will be given in more detail of a method of performing a plurality of sensing operations using the skin measurement device 100 and a method of extracting skin-related information using a plurality of sensing results generated by the plurality of sensing operations.

Referring to FIGS. 4, 5A and 5B, the skin measurement device 100 of the present invention may perform sensing at a plurality of points on a specific skin, on the basis of a movement of the skin measurement device 100 due to an external force while it is brought into contact with the skin (S310). Accordingly, the controller 180 may sense (acquire) a plurality of pieces of information related to the skin for each of the plurality of points of the skin. Here, the plurality of pieces of information related to the skin may be a plurality of sensing results for the skin. In addition, the sensing result (information related to the skin) may be intensity of light reflected at different depth from each point of the skin.

For example, as illustrated in FIG. 5A, when sensing is performed at three points on a specific skin, the controller 180 may acquire a sensing result including P1, a sensing result including P2 and a sensing result including P3.

Here, the sensing results including P1, P2, and P3 may be sensing results measured at different points of the skin, respectively. For example, the sensing result including P1 may be intensity of light reflected for each depth from a first point of the skin, the sensing result including P2 may be intensity of light reflected for each depth from a second point of the skin, and the sensing result including P3 may be intensity of light reflected for each depth from a third point of the skin.

In addition, P1, P2, and P3 may denote intensity of light reflection on the first, second, and third points of the skin. Here, the sensing results including P1, P2, and P3 are shown based on a depth axis for convenience of explanation. However, the sensing results including P1, P2, and P3 may be understood as being present on a surface axis (not illustrated) perpendicular to the depth axis and an OCT intensity axis, respectively (3D).

The controller 180 may determine a point, which has the greatest intensity of light for each skin-related information (intensity of reflected light for each depth) obtained at each of the plurality of points of the skin, as light reflection intensity (P1, P2, P3) of each point.

Here, the difference of the OCT intensities (light reflection intensity) at P1, P2, and P3 results from sweat glands, sebaceous matters, and flexion in the skin. That is, the intensities of P1, P2, and P3 depend on a state of a skin surface at the first, second, and third points of the skin.

Thereafter, the controller 180 may merge the plurality of sensing results, which have been sensed at the plurality of points on the skin by the movement, in a preset manner.

Specifically, the controller 180 may merge the plurality of sensing results sensed at the plurality of points so that the light reflection intensity information on each skin surface, of the light reflection intensity information included in each of the plurality of sensing results, can coincide with each other (S320).

Referring to FIGS. 5A and 5B, the controller 180 may merge the plurality of sensing results sensed at the plurality of points on the skin by the movement in a manner that intensities of light reflected from the respective skin surfaces included in the plurality of sensing results (i.e., light reflection intensity information at each surface) (P1, P2 and P3) can coincide with each other. Here, a criterion of the merging may be a point (for example, P1) with the greatest intensity of light reflected from the surface.

For example, as illustrated in FIG. 5A, when the plurality of sensing results are obtained in response to the sensing operation being performed at the plurality of points by the movement of the skin measurement device, as illustrated in FIG. 5B, the controller 180 may merge (or align) the plurality of sensing results such that the light reflection intensities P1, P2 and P3 at the skin surfaces included in the plurality of sensing results can coincide with each other.

Thereafter, the controller 180 may extract the skin-related information using the merged plurality of sensing results (S330).

Hereinafter, description will be given in more detail of a method of extracting the skin-related information using the merged plurality of sensing results (fitting curve), with reference to the accompanying drawings.

FIG. 5B illustrates a graph in which a plurality of sensing results are merged. Meanwhile, the graph including R illustrated in FIG. 5B may be a factor for determining an interface between the subcutaneous fat layer and the dermis of the skin.

A value of the graph including the R may be extracted for each depth. Specifically, the R value may be extracted by {1−(distribution between the plurality of sensing results and fitting curve (the merged plurality of sensing results)/distribution of the plurality of sensing results}).

Since the subcutaneous fat layer of the skin has various elements and structures of the subcutaneous fat layer, the subcutaneous fat layer has a larger difference in the light reflection intensity at the different depth on each point of the skin than the dermis. As a result, the distribution between the plurality of sensing results and the merged plurality of sensing results (fitting curve) becomes large, so that the R value becomes small.

The controller 180 may designate the largest value among the R values as DE2, that is, depth corresponding to the interface between the dermis and the subcutaneous fat layer.

Hereinafter, description will be given in detail of a method of extracting skin-related information (surface reflectance of the skin, an epidermal thickness of the skin, a light attenuation rate in the epidermis of the skin, a light attenuation rate in the dermis of the skin, an average light attenuation rate in the epidermis and the dermis of the skin, etc.), with reference to FIG. 6.

First, the controller 180 may extract light reflectance on a surface of a specific skin with which the skin measurement device 100 is brought into contact (S322). Specifically, the controller 180 may extract, from the merged plurality of sensing results, intensity of light at a point with the greatest intensity of intensities of light reflected from the specific skin as light reflection intensity on the surface of the skin. The controller 180 may extract the light reflectance on the surface using intensity of light emitted to the skin and the light reflection intensity on the surface of the skin.

The controller 180 may calculate an R value and an inclination of the merged plurality of sensing results for each depth of the skin (S334). Here, the controller 180 may calculate a linear regression function for the merged plurality of sensing results, and calculate the inclination using the linear regression function.

The controller 180 may detect a point having an R value of Max from a point with a great depth and set it to DE2 (S336). Here, DE2 may refer to an interface (or depth of the interface) between the dermis and the subcutaneous fat layer.

The controller 180 may extract a point at which the inclination is converted from DE2, and set the extracted point to DE1 (S338). Here, extracting the converted point of the inclination from DE2 may refer to detecting the point at which the inclination is converted while moving from a depth corresponding to DE2 toward the surface (hereinafter, it will be equally applied to similar expressions). Referring to FIG. 5B, converting the inclination may refer to changing the inclination to a reference value (magnitude) or more (for example, converting a negative value to a positive value). Here, DE1 may refer to an interface (or depth of the interface) adjacent to the epidermis of the interface of the dermis.

Specifically, an arbitrary layer may be formed between the dermis and the epidermis. Accordingly, there may be a portion where the inclination changes from negative to positive. When an arbitrary layer present between the dermis and the epidermis is thinner than a reference thickness or is not present, DE1 may refer to the interface (or depth of the interface) between the dermis and the epidermis.

Thereafter, the controller 180 may extract an inclination between DE1 and DE2 (S340). The inclination between DE1 and DE2 may refer to a light attenuation rate in the dermis of the specific skin.

The controller 180 may then set a point, at which the inclination is converted from DE1, to EP2 (S342). The EP2 may refer to an interface adjacent to the dermis of the interface of the epidermis (or an interface of the arbitrary layer present between the epidermis and the dermis/epidermis). The controller 180 may determine a point, at which the inclination from DE1 changes to a reference value (magnitude) or more (for example, a point converted from positive to negative), to EP2. Similarly, when an arbitrary layer present between the dermis and the epidermis is thinner than a reference thickness or is not present, the EP2 may refer to the interface (or depth of the interface) (or DE1) between the dermis and the epidermis.

In addition, the controller 180 may set a feature point (point), at which the inclination from the surface of the skin changes to a reference value (magnitude) or more, to EP1 (S344). That is, the controller 180 may detect a feature point at which the inclination changes to a reference value (magnitude) or more while going from the surface of the skin in a depth direction, and set the feature point to EP1. As another method, the controller 180 may alternatively detect a feature point at which the inclination changes to the reference value or more while coming from the EP2 toward the surface.

The controller 180 may extract the inclination between EP1 and EP2 (S346). The inclination between EP1 and EP2 may refer to a light attenuation rate in the epidermis of the skin.

Further, the controller 180 may extract the inclination between EP1 and DE2 (S348). The inclination between EP1 and DE2 may refer to an average light attenuation rate in the epidermis and dermis of the skin.

Further, the controller 180 may extract a distance between EP2 and the surface (S350).

Here, the epidermal thickness is extracted as the distance from the surface to EP2. However, extracting the light attenuation rate in the epidermis as the inclination between EP1 and EP2 is to minimize noise of sweat glands, sebaceous matters, and flexion in the skin With such configuration, the controller 180 may extract (sense) the information related to the specific skin brought into contact with the skin measurement device 100 (e.g., light reflectance on the surface of the skin, the light attenuation rate in the epidermis, the light attenuation rate in the dermis, the average light attenuation rate in the epidermis and dermis, the epidermal thickness, etc.).

Meanwhile, the controller 180 may also measure an amount of melanin of the skin using the skin-related information. The amount of melanin of the skin may be included in the skin-related information. The amount of melanin of the skin may be sensed based on an absorption rate of light, which is extracted based on intensity of light emitted to the skin and intensity of light reflected from the skin.

The method described in FIG. 6 is not limited to a time-series, but may be performed in any order. For example, the method may be implemented as a method of obtaining a light attenuation rate in the dermis after detecting DE2 and DE1 from a point with a great depth, and obtaining a light attenuation rate in the epidermis after detecting EP2 and EP1, or as a method of obtaining the light attenuation rate in the dermis and the light attenuation rate in the epidermis after detecting all of DE2, DE1, EP2 and EP1.

With this configuration, in the present invention, information related to skin having different characteristics can be extracted for each user and for each portion of the skin. In addition, the skin measurement device of the present invention may transmit the skin-related information to the skin treatment device, and guide the skin treatment device to determine output information of a laser optimized for the measured skin-related information.

Meanwhile, in the present invention, information corresponding to a position (portion) of a specific skin, measured by the skin measurement device, of a portion of a body, may be transmitted to the skin treatment device together with the sensed skin-related information.

Hereinafter, description will be given in more detail of a method of transmitting both of information related to a specific skin of a body, sensed by the skin measurement device, and information corresponding to a position of the sensed skin, with reference to FIG. 7.

Figure 7:
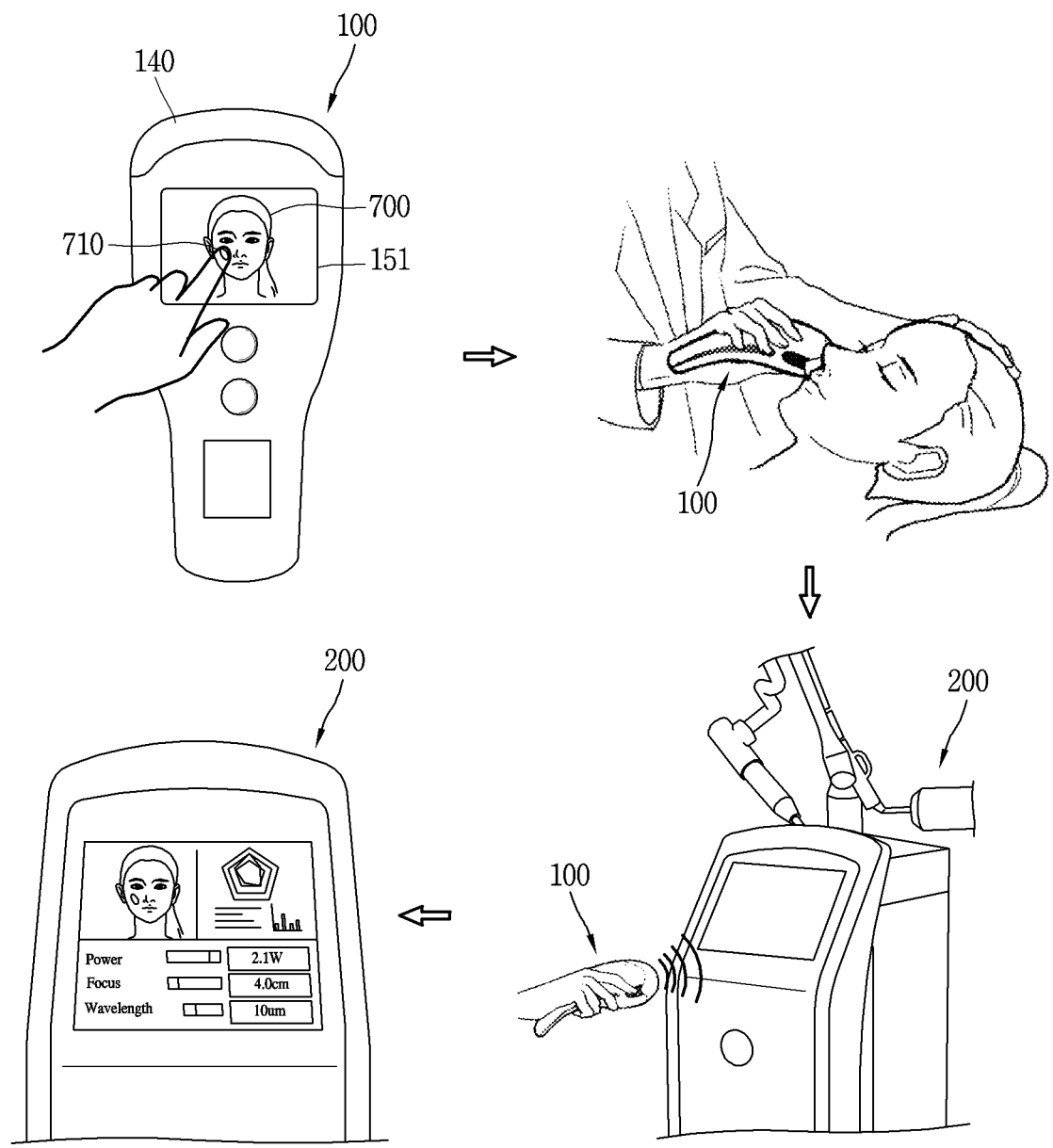
FIG. 7 is a conceptual view illustrating a method in which a skin measurement device transmits skin-related information to a skin treatment device in association with information related to a portion of a body in accordance with one embodiment of the present invention.

Referring to FIG. 7, an image 700 that guides a user to select a part of a body may be output on the display unit 151 of the skin measurement device 100 according to the present invention. That is, the controller 180 may control the display unit 151 to output the image 700 for guiding the selection of the part of the body.

The image 700 displayed on the display unit 151 may be stored in the memory. Further, the image 710 may be any image as long as it is an image related to the body. For example, as illustrated in FIG. 7, the image 700 may be a face image, and, although not illustrated, may also be an image such as an arm, a body, a back, a leg, etc. The image 710 may be displayed on the display unit 151 based on a user request or may be displayed on the display unit 151 by satisfaction of a preset condition. For example, the preset condition, for example, may include conversion from power-on to power-off of the skin measurement device 100, movement of the skin measurement device 100 corresponding to a preset pattern, or the like.

The controller 180 may sense a touch applied to the image 700 displayed on the display unit 151. The controller 180 may determine based on the touch that at least part of the image 700 has been selected.

When the skin measurement device is brought into contact with the skin after the at least part 710 of the image 700 is selected, the controller 180 may sense information related to the contacted skin. That is, the selection of the at least part 710 of the image 700 may be performed before the skin measurement device 100 is brought into contact with the skin, that is, before performing the sensing operation. However, the present invention is not limited to this. Selecting the at least part 710 of the image 700 may also be performed during the sensing, after completing the sensing, or before transmitting the sensed information related to the skin to the skin treatment device.

Then, the controller 180 may also transmit information corresponding to the selected at least part of the image when the measured information related to the skin to the skin treatment device 200 in response to satisfaction of the preset condition.

For example, as illustrated in first and second drawings of FIG. 7, when the skin-related information 100 is brought into contact with a specific skin (e.g., a skin of a right cheek) after the at least part 710 (e.g., the right cheek) of the image 700 displayed on the display unit 151 is selected, the controller 180 may sense information related to the skin. Afterwards, the controller 180, as illustrated in a third drawing of FIG. 7, may transmit the sensed information related to the skin to the skin treatment device 200 together with the information corresponding to the at least part 710 (the right cheek) of the image 700, in response to satisfaction of a preset condition.

When receiving the sensed information related to the skin and the information corresponding to the at least part 710 transmitted from the skin measurement device 100, the skin treatment device 200 may decide output information of a laser based on the skin-related information and a table stored in the memory.

In addition, the controller 180 may output information related to a portion to be treated with the laser, as the decided output information of the laser, based on the information corresponding to the at least part 710.

In addition, the display unit 151 of the skin treatment device may display the decided output information of the laser and the information related to the portion to be treated with the laser.

In addition, the skin treatment device 200 may store in a memory thereof at least one or combination of the information related to the portion to be treated with the laser, the information corresponding to the at least part 710, the sensed information related to the skin, user information receiving the skin treatment, and a time (date) to perform the skin treatment.

As described above, according to the present invention, a skin measurement device of the present invention can measure information related to a specific skin to be treated, namely, light reflectance on a surface of the skin, a light attenuation rate at the epidermis of the skin, a light attenuation rate at the dermis of the skin, an epidermal thickness and the like and transmit the measured information to a skin treatment device, which may enable an optimized skin treatment at the skin treatment device. Accordingly, the present invention provides an effect that an optimized skin treatment can be performed by recognizing (detecting, determining) a skin characteristic for each user.

In addition, the skin measurement device according to the present invention can extract information related to the skin based on sensing results obtained at a plurality of points of the skin, which may allow an extraction of more accurate skin conditions, i.e., the information related to the skin.

In addition, the skin measurement device according to the present invention can transmit the skin-related information to the skin treatment device, in response to satisfaction of a preset condition. Thus, according to the present invention, an effect of enhancing user convenience in performing a skin treatment can be obtained.

In addition, the skin measurement device according to the present invention can output an image guiding a selection of a part of a body. Also, when the skin measurement device is brought into contact with the skin after at least part of the image is selected, the skin measurement device can transmit the skin-related information to the skin treatment device together with information corresponding to the selected at least part of the image. Accordingly, the present invention can provide a new user interface that allows information related to the portion (skin) of the body measured using the skin measurement device to be output on or stored in the skin treatment device.

The invention claimed is:

1. A skin measurement device capable of performing data transmission and reception with a skin treatment device, the skin measurement device comprising:
   a sensing unit configured to sense information related to skin; and
   a controller configured to control the sensing unit to sense information related to skin when the skin measurement device is brought into contact with the skin,
   wherein the sensing unit emits light to the skin, and senses the information related to the skin based on reflected light from the skin,
   wherein the controller is further configured to perform a plurality of sensing operations and extract the information related to the skin based on a plurality of sensing results of the plurality of sensing operations,
   wherein the controller is further configured to merge the plurality of sensing results obtained at a plurality of points on the skin by a movement in a preset manner to generate merged sensing results, and extract the information related to the skin using the merged sensing results,
   wherein each of the plurality of sensing results includes light reflection intensity information corresponding to a skin depth for each point of the skin, and
   wherein the controller is further configured to:
   determine a point, which has a greatest intensity of light for each skin-related information obtained at each of the plurality of points of the skin; and perform the merge of the plurality of sensing results sensed at the plurality of points on the skin by the movement in a manner that the greatest intensities of light reflected from respective skin surfaces included in the plurality of sensing results coincide with each other, wherein a criterion of the merge is a point with the greatest intensity of light reflected from respective skin surface.

2. The skin measurement device of claim 1, wherein the information related to the skin sensed by the sensing unit includes at least one of light reflectance at a surface of the skin, a light attenuation rate in the epidermis of the skin, a light attenuation rate in the dermis of the skin, and an epidermal thickness.

3. The skin measurement device of claim 2, wherein the sensing unit comprises a light source configured to:

emit a first part of light the skin and a second part of light to a mirror provided therein, and sense the information related to the skin using interference between light reflected from the skin and light reflected from the mirror.

4. The skin measurement device of claim 1, wherein the controller transmits the sensed information related to the skin to the skin treatment device based on satisfaction of a preset condition, and wherein the preset condition is at least one of a case where an elapsed time after the skin measurement device is brought into contact with the skin exceeds a preset time, a case where the skin measurement device is moved by a preset distance in the contact state with the skin, and a case where the skin measurement device in the contact state with the skin is separated from the skin.

5. The skin measurement device of claim 1, further comprising a display unit configured to output an image guiding a selection of a part of a body, wherein the controller is further configured to transmit the sensed information related to the skin together with information corresponding to at least part of the image when the at least part of the image is selected and the skin measurement device is brought into contact with the skin.

* * * * *